United States Patent [19]

Wagner et al.

[11] 4,016,209

[45] Apr. 5, 1977

[54] 3-[N'-(3-HALOPROPYL)-N-'-METHYLAMINO]-N,N,N-TRIMETHYL-1-PROPANAMINIUM HALIDE AND ACID ADDITION SALTS THEREOF

[75] Inventors: Arthur F. Wagner, Princeton; Tsung-Ying Shen, Westfield, both of N.J.

[73] Assignee: Merck & Co., Inc., Rahway, N.J.

[22] Filed: Apr. 23, 1975

[21] Appl. No.: 570,910

[52] U.S. Cl. .................. 260/567.6 M; 260/501.15; 260/567.6 P; 260/465.5 R; 260/501.12; 424/329; 260/501.1 B

[51] Int. Cl.² .......................................... C07C 89/30

[58] Field of Search ............ 260/567.6 M, 567.6 R, 260/501.15; 424/329

[56] References Cited

UNITED STATES PATENTS 3,147,065  9/1964   Koshar et al. .............. 260/567.6 M
3,493,615  2/1970   Bauman ....................... 260/501.15
3,721,706  3/1973   Hoffmann et al. ......... 260/567.6 M
3,834,867  10/1974  Matter et al. .............. 260/567.6 M

*Primary Examiner*—Bernard Helfin
*Assistant Examiner*—James H. Reamer

[57] ABSTRACT

Novel linear, unbranched, non-cross-linked polymers particularly poly-[{methyl-(3-trimethylammoniopropyl)imino} trimethylene dihalide] are prepared by the polymerization of the novel monomer, 3-[N'-(3-halopropyl)-N'-methylamino]-N,N,N-trimethyl-l-propanaminium halide, or an acid addition salt thereof preferably in an oxygen excluded environment, e.g., under nitrogen or argon. The polymer, especially after modification of terminal groups, is an excellent oral anticholesterolemic.

10 Claims, No Drawings

3-[N'-(3-HALOPROPYL)-N-'-METHYLAMINO]-N,N,N-TRIMETHYL-1-PROPANAMINIUM HALIDE AND ACID ADDITION SALTS THEREOF

DISCLOSURE OF THE INVENTION

This invention relates to novel linear, non-cross-linked, non-branched polymers and their preparation by the polymerization of a novel monomer. The term "non-branched" is intended herein to indicate a polymer having no repeated monomer units extending from the polymer backbone; the term linear is intended to define a polymer having a straight chain and the term "non-cross-linked" is used in its usual sense.

More particularly, this invention relates to the preparation of a 3-[N'-(3-halopropyl)-N'-methylamino]N,N,N-trimethyl-1-propanaminium compound of the formula:

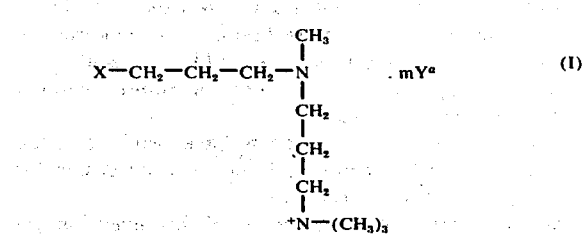

where X chloro, chlori, bromo, or iodo, Y is a pharmaceutically acceptable anion and preferably is chloride, bromide or iodide and is most preferably the same as X, together with acid addition salts thereof.

In the compounds of formula I, $a$ is the anionic charge on Y, $m$ being a number such that the product of $m$ and $a$ is 1.

This invention is also concerned with the polymer prepared from monomer I, which is a poly-[{methyl-(3-trimethylammoniopropyl)imino}trimethylene] compound having the structural formula:

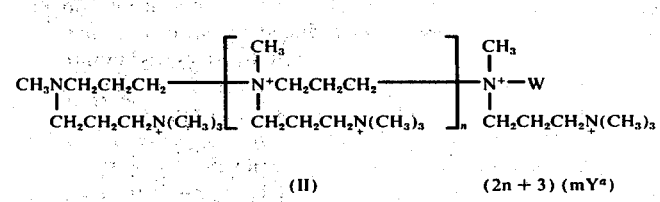

where Y, $m$, and $a$ are as above defined; $n$ is an integer such that the number average molecular weight of polymer II is greater than about 2,000; and W is 3-halopropyl, 3-hydroxypropyl, or allyl. The proportion of end groups W that are 3-halopropyl, 3-hydroxypropyl, or allyl varies and depends upon the conditions of the polymerization reaction since the latter will determine the extent and nature of the displacement of the chloro moiety of the end groups.

As reaction time or temperature increase, the proportion of hydroxypropyl end groups or allyl end groups compared to halopropyl end groups likewise increases. Conversely, with shorter reaction times or with lower reaction temperatures the proportion of halo end groups displaced is decreased.

Generally, there can be from about 10 to 80% by weight of polymer II terminating in hydroxypropyl and from 5 to 90% terminating in halopropyl, any remainder being the allyl terminal group. The hydroxypropyl end group is satisfactory from a utility standpoint, but is not a wholly desired moiety since it represents a terminal polymer group that cannot undergo further polymerization during reaction with monomer I, and therefore prematurely terminates chain growth. Termination in a haloproyl group is termination in a group which potentially can undergo further chain growth, but for exhaustion of monomer I or other reasons. The allyl group represents elimination of HX and likewise is a terminal group that can undergo no further polymerization. In essence then these three species are the result of randomly occurring reactions during polymerization of monomer I.

This invention is particularly concerned with the end group modified polymer III in which the 3-halopropyl end groups have been modified by displacement of the halo moiety by hydrogen, alkylthio or triloweralkylammonio functions. Said end group modified polymer prepared from polymer II is a poly-[{methyl-(3-trimethylammoniopropyl)imino}trimethylene] compound having the structural formula:

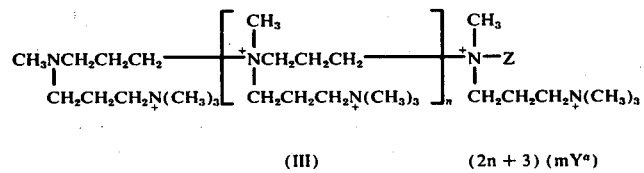

where Y, $m$, $n$, and $a$ are as defined above and Z may be 3-trimethylammoniopropyl associated with one equivalent of $Y^a$ counter anion, 3-(2-naphthylthio)propyl, 3-benzenethiopropyl, 3-hydroxypropyl, propyl or allyl. The proportion of end groups Z that are 3-hydroxypropyl or allyl is largely dependent upon the nature of the end groups W in the precursor polymer II. In preferred embodiments of polymer III $n$ is generally greater than 10 so that the number average molecular weight is from about 4,000 to 16,000, although the molecular weight of individual species can range from 600 to 20,000. The molecular weight of polymers II and III is established by the titration of the unique tertiary amine end group, by gel permeation chromatography and measurement of intrinsic viscosity. As determined by titration, rather consistent number average molecular weights of about 5,000 are obtained, whereas gel permeation indicates average molecular weights of about 14,000 and higher.

Polymers II and III are useful as antistatic agents, antimicrobial agents, flocculating agents, agents for coating paper to render it electroconductive, and nonabsorbable gastrointestinal bile acid binding agents. This latter property makes polymers II and III particularly valuable since the sequestration of bile acids in man is known to reduce levels of blood serum cholesterol. Because of their water solubility and their linear, unbranched, non-cross-linked structure and their high charge to mass ratio, polymers II and III are the most efficient bile acid sequestrants available. Polymer III is particularly noteworthy in this respect since its end groups Z make it safer and more acceptable pharmaceutically for chronic administration to lower blood serum cholesterol levels.

All available evidence indicates that the incidence of higher than normal blood serum cholesterol levels in humans (especially in so-called Type II Frederickson patients) is associated with atherosclerosis and other hypercholesteremic disease signs. Atherosclerosis is manifested by the effects of occlusion of the circulation, giving rise to coronary, cerebrovascular, and some forms of peripheral vascular diseases and it is the leading cause of death in many countries.

In an effort to reduce the incidence of atherosclerosis, elevated blood serum cholesterol levels are the target of various control measures, including restricted and special dietary intake, inhibition of cholesterol synthesis, accelerated catabolism, prevention of gastrointestinal absorption, as well as by means of binding bile acids in the gastrointestinal tract. This latter technique is highly favored since it requires neither surgical intervention nor sudden and severe changes in dietary habits or lifestyle of patients.

The exact means by which gastrointestinal bile acid binding accomplishes a lowering of blood serum cholesterol levels is, however, unknown; it is believed feedback mechanisms effect cholesterol oxidation responses depleting serum cholesterol in an effort to restore bile acid levels. Regardless of the uncertainty of its mechanism, the technique is well accepted. What is lacking is a convenient, efficient, non-toxic, and easily tolerated binding agent.

Heretofore, a variety of bile acid binding agents have been employed. These include iron salts which produce insoluble precipitates with bile acids, organic bases to act similarly, and polymers having a salt-forming capability. Absorbable precipitants, however, present acute and chronic toxicity hazards. The use of non-absorbable highly cross-linked polymers to avoid such toxicity problems has not provided a suitable alternative, because the average effective adult daily dose of such polymers heretofore employed ranges up to 40 grams; the cross-linking effectively prevents access to a large number of potential binding sites and drastically reduces efficiency. The physical bulk of such a dose, especially when of a water-insoluble cross-linked resin, can induce partial blockage of the gastrointestinal tract and an unpleasant, heavy sensation. Furthermore, any objectionable odor and taste of so large a dose is difficult to mask.

Gel-type compositions which have less cross-linking and are branched, as that term is heretofore defined, swell markedly on water sorption, and although relatively free of abrasive irritation, often cause pressure discomfort.

Water-soluble polymers heretofore proposed for use as bile acid binding agents cause very high viscosities in solution, and have marked astringent action in the oral cavity. Furthermore, they present much bulk for consumption, retaining as much as an equal weight of water in dry form. Most seriously, they can be degraded in the gastrointestinal tract.

Consequently, there has been only limited benefit derived from treatment by this method, although the incidence of disease linked to hypercholesteremia is extremely high and continues to rise alarmingly.

Several explanations are advanced for the inability of resins heretofore suggested for use in hypercholesterolemics to match bile acid uptake with the efficency of chloride ion capture. One view holds that smaller inorganic anions can reach binding sites more readily than the bile acid anion. Therefore, to make a more efficient resin one should provide greater separation of binding sites to accommodate bulky acids. Another view holds that resins need to be more lipid-like to penetrate in vivo micelle formations holding fat-like bile acids, thus leading to suggestions that decreased water solubility for resins was desirable.

Unfortunately, these concepts have produced little improvement when translated into polymer design for treating hypercholesterolemia.

We now find that the polymers of this invention are exceptionally efficient agents for treating hypercholesterolemia and have the extremely important advantage that their end groups present no known toxicity potential.

Monomer I is synthesized by one of the following three alternative methods.

It is most suitably obtained by the following route. 3-Bromo-N,N,N-trimethyl-1-propanaminium halide is reacted with methylamine in an inert solvent, e.g., alkanols such as ethanol or methanol, dimethylformamide, water or mixtures thereof at temperatures from 0° C. to 30° C. for from 4 to 24 hours. The term inert solvent used in this and following instances signifies that the solvent does not react with the other reactants or products thereof.

The product N,N,N-trimethyl-[3-(methylamino)]-1-propanaminium halide hydrobromide is suspended in a suitably inert solvent, preferably methanol, ethanol or water, and an equivalent of base, preferably an alkali or alkaline earth hydroxide or alkali carbonate is added slowly during a period of from 10 minutes to 5 hours. The temperature is maintained at 0° C. to 50° C. during the addition of alkali. The reaction mixture is concentrated to dryness under reduced pressure, and the product N,N,N-trimethyl-[3-(methylamino)]-1-propanaminium halide is extracted from the residue with a suitable solvent such as acetonitrile.

The product N,N,N-trimethyl-[3-(methylamino)]-1-propanaminium halide may be purified by recrystallization from an alkanol-ether solvent mixture, e.g., isopropanol-diethyl ether or it may be used without further purification in the next step in which it is treated in aqueous solution with from 1.1 to 3 equivalents of oxetane in a sealed vessel at a temperature of from 50° C. to 150° C. for a period of from 10 to 24 hours. The product is isolated by concentration of the reaction mixture to dryness and extraction into a suitable solvent such as acetonitrile from which it crystallizes on evaporation of the solvent. The product, 3-[N'-(3-hydroxypropyl)-N'-methylamino]-N,N,N-trimethyl-1- propanaminium halide may be purified by recrystallization from acetonitrile.

Prior to the conversion of the 3-hydroxypropyl function to a 3-halopropyl moiety, the intermediate 3-[N'-3-hydroxypropyl)-N'-methylamino]-N,N,N-trimethyl-1-propanaminium halide may be suitably converted to a propanaminium analog. Most preferably this analog bears the same halide counter anion as the halo moiety that will displace the hydroxyl function of the hydroxypropyl moiety, although other counter anions $Y^a$ are suitable. The conversion is accomplished by passing an aqueous solution of the 1-propanaminium halide intermediate acidified with an appropriate acid through an appropriate anion exchange resin in the desired anionic form.

Alternatively, the halide anion of the intermediate may be exchanged for $OH^-$, which in turn may be acidified with HY or exchanged for $Y^a$ by passage of an appropriately neutralized solution through an anion exchange resin on the $Y^a$ cycle.

Concentration of the aqueous eluate to dryness yields the desired intermediate, which on treatment with an appropriate halogenating agent such as thionyl chloride, phosphorus oxychloride, phosphorus pentachloride, thionyl bromide or phosphorus pentabromide yields a 3-[N'-(3-halopropyl)-N'-methylamino]-N,N,N-trimethyl-1-propanaminium halide acid addition salt. The product is usually purified by concentration of the reaction mixture and leaching of the residue with an appropriate ether solvent. The residue is taken up in water, and the solution is treated with activated carbon. The aqueous solution is then filtered and concentrated to dryness under reduced pressure and crystallized from a mixed solvent such as isopropanol-acetone.

In a second alternative process, monomer I may be synthesized in one step by treating N,N,N-trimethyl-[3-(methylamino)]-1-propanaminium halide with one equivalent of a 1,3-dihalotrimethylene compound such as 3-chloro-1-iodopropane, 3-bromo-1-chloropropane, or 1,3-dibromopropane, in an inert solvent such as acetonitrile. Insoluble byproducts are removed by filtration, the reaction mixture is concentrated to dryness, and the product is extracted from the residue with an appropriate solvent such as chloroform or methylene chloride. Counter anion exchange may be accomplished as described above and the product may be crystallized from isopropanol-ether or isopropanol-acetone mixtures.

In a third alternative synthesis of monomer I, 3-aminopropanol is added to acrylonitrile yielding 3-(2-cyanoethyl)aminopropanol, which in turn is converted in two steps to 3-[N-(2-cyanoethyl)-N-formylamino]-propanol. The nitrile function of the latter is catalytically reduced to a primary amine function which in turn is exhaustively alkylated with a methyl halide to yield a 3-[N'-formyl-N'-(3-hydroxypropyl)amino]-N,N,N-trimethyl-1-propanaminium halide. Reduction of the formyl moiety in the latter to a methyl function is accomplished by treating this intermediate with a formic acid-formalin mixture at 60° C.–100° C. for 10–24 hours, followed by acidification with the appropriate aqueous hydrogen halide and concentration to dryness yielding a 3-[N'-(3-hydroxypropyl)-N'-methylamino]-N,N,N-trimethyl-1-propanaminium halide hydrohalide. Conversion of this intermediate to 3-[N'-(3-halopropyl)-N'-methylamino]-N,N,N-trimethyl-1-propanaminium halide hydrohalide is accomplished as described in our preferred synthesis of monomer I above, and anion exchange, if desired, is effected by any of the heretofore described procedures.

Polymer II is obtained through the head to tail polymerization of monomer I, preferably in an oxygen excluding environment by the treatment of an acid addition salt of monomer I with one equivalent of an aqueous alkali hydroxide or by the polymerization of monomer I as a free base in aqueous solution. Generally, if the acid addition salt of monomer I is employed, the bulk of the resulting neutralization salt is removed prior to polymerization. The polymerization is itself conducted in an aqueous medium usually 3 to 10 molar in monomer I. The reaction medium comprising monomer I and water is heated in an oxygen excluding atmosphere, usually under nitrogen or argon, to a temperature of from 80° C.–110° C. for a period of from 6 to 60 hours. Temperatures in excess of 100° C. can be employed with pressurization techniques. The reaction is most preferably conducted at 100° C. with a 6–8 molar aqueous solution of monomer I for 12–18 hours under nitrogen. The product is rid of salt and low molecular weight materials by ultrafiltration of a 5% aqueous solution in Amicon Filter Cells equipped with UM10 Diaflo Ultrafilters at constant volume and 60 psi pressure. The purified polymer is isolated from the aqueous retentate by concentration under reduced pressure at temperatures up to 50° C. The product is usually ground to a fine powder and dried under reduced pressure over phosphoric anhydride.

The remaining chloro end groups of polymer II are displaced by one of three methods to yield polymer III. These conversions are carried out in aqueous solution and preferably at room temperature or lower to minimize partial degradation of the polymer that might occur in alkaline reaction media. For conversion of the 3-chloropropyl end group to a 3-trimethylammoniopropyl halide end group, polymer II is dissolved in a small amount of water and treated for 8 to 24 hours with a large excess of 6M trimethylamine in water. The product is isolated by concentration of the reaction medium to dryness at reduced pressure and temperatures not exceeding 30° C. The product may be ground to a powder and dried under reduced pressure or it may be subjected to a preliminary purification by ultrafiltration of a 5% aqueous solution of the isolated polymer followed by concentration of the retentate to dryness under reduced pressure.

Alternatively, the chloro moiety of the 3-chloropropyl end groups of polymer II may be displaced by naphthylthio or benzenethio moieties in aqueous solution. An aqueous solution of the polymer is treated with up to a two-fold excess of the sodium salt of either a naphthylthiol or benzenethiol at room temperature for from 12 to 48 hours. Next an amount of acid equivalent to the sodium mercaptide is added and the unreacted thiol reagent is removed by filtration or extraction of the reaction medium with an appropriate solvent such as diethyl ether or chloroform. The aqueous solution of polymer III is usually purified by ultrafiltration, concentration of the retentate under reduced pressure, and drying over phosphoric anhydride under reduced pressure.

For the displacement of the chloro end group of polymer II by hydrogen, an aqueous solution of polymer II and two equivalents of a base is reduced over a noble metal catalyst at room temperature until the appropriate hydrogen uptake is recorded. Potassium acetate is a preferred base and 5% palladium on carbon is a preferred catalyst to effect the conversion. In general, a reaction time of two days is required for reductions carried out at 40 psi of hydrogen. The product is usually purified by ultrafiltration and changes in counteranion composition owing to the base used are adjusted by passage of the retentate through a column of Dowex 1 X-2 anion exchange resin on the appropriate anion cycle. The product is usually isolated by concentration of the aqueous solution to dryness under reduced pressure.

The anions on polymers II and III are generally limited to halide by the techniques of the prior steps. The full range of polymers where the anion differs from halide can be obtained by dissolving polymer II or III having a halide anion in water, alcohol, or mixtures thereof in any proportion and passing the solution through a bed of anion exchange resin, either a synthetic or a zeolite type, where the halide ion is exchanged and replaced by $Y^a$. The anion exchange method employing a resin technique can be direct, that is, exchanging halide ion for $Y^a$ or one can first exchange halide ion for $OH^-$ and then either by a subsequent ion exchange or simple neutralization, exchange $OH^-$ for $Y^a$.

Additionally, chemical exchange techniques can be employed when a precipitate of a metal halide is less soluble than the added slightly soluble metal salt MY. The precipitated metal halide can then be filtered from the soluble polymer II or III.

A simple example of the latter technique involves treating a solution of polymer II or III containing the bromide counter ion with an excess of freshly precipitated silver chloride. After the halide anion exchange is complete, the mixture of silver chloride and silver bromide is removed by filtration leaving a solution of polymer II or III containing the chloride counter ion. Alternatively, polymer II or III where $Y^a$ is sulfate can be treated with solutions of water soluble calcium or barium salts. Thus, sulfate can be replaced with nitrate and the precipitate of barium sulfate removed.

Throughout this description, $Y^a$ represents an anion which counters the charge on the quaternized imino group, and thus can be a monovalent anion. It is to be understood, however, that $Y^a$ is contemplated to include polyvalent anions where one anion can counter the charge on more than one charged imino group. Thus, $Y^a$ can include anions of inorganic acids, as well as of organic acids such as, for example, halide, e.g., chloride, bromide, or iodide; sulfate; bisulfate; phosphate; acetate; ascorbate; citrate; hydroxycitrate; carbonate; bicarbonate; nicotinate; glycinate; taurinate; salicylate; and other anions derived from physiologically non-toxic acids, especially salts of physiologically active acids such as those derived from clofibrate and halofenate, i.e., 2-(p-chlorophenoxy)-2-methylpropionic and 3-trifluoromethylphenoxy-(4-chlorophenyl)-acetic acids. When such anions of physiologically active compounds are used to neutralize quaternized imino groups, it is apparent that only a portion of the charged imino groups may be so neutralized. The amount of anion from the physiologically active compound is apportioned in a ratio such that the amount administered with the polymer dosage can fall within the desired range for the physiologically active compound.

Effective lowering of cholesterol blood levels is obtained by the oral administration of remarkably small dosages of the polymers of this invention. This enables a flexibility of formulation previously unavailable. The polymers can be finely divided powders and suitably used as such or preferably admixed with varying amounts of solid carrier agents such as colloidal silica, starches, sucrose, talc, lactose, cellulose, or modified cellulose, dry milk powder, protein powders such as soy flour, and the like. These are preferably made into unit dosage forms such as tablets, filled gelatin capsules or a foil or paper envelope containing the premeasured dose which can include supplementary vitamins and minerals, and which can be readily torn open and added to edible liquids such as fruit juices or other beverages. The unit dose composition may comprise from 10% to 99% by weight of polymer, the remainder being carriers, flavorings, excipients, flow agents and the like. In such a unit dose, the active polymer may comprise from 0.1 gm. to up to 10 gms. in powder packets.

Also suitable are aqueous solutions or suspensions which can be prepared and are preferably sweetened or flavored. Although not entirely desirable, the polymers can be mixed in various vehicles such as safflower or corn oil for oral ingestion as such or as an aqueous emulsion. These may also be encapsulated.

The total daily dosage of bile acid binding polymer is preferably divided into three or four equal portions and taken before each meal and prior to bedtime. This regimen provides for maximum resin contact time during periods of highest intestinal bile acid concentrations.

The polymers of this invention may be used alone, or, if desired, can be compounded together with triglyceride synthesis inhibitors or other bile acid binding agents for particular treatments. In addition, as heretofore stated, the polymers described herein form salts with the acids of clofibrate and halofenate, which salts are useful in cardiovascular disease therapy. The following examples are illustrative of the dosage forms which can be employed in the practice of our invention. Those skilled in the art of pharmaceutical compounding will be aware of variations which can be practical without departing from the spirit of our invention. It is anticipated that multiple dosages, e.g., two or three tablets or capsules can be taken at one time if higher dosages are prescribed.

Additional ingredients which may comprise the carrier portion of the compositions of this invention, can also have pharmacological activity and can include other choleretic agents such as tocamphyl florantyrone; taurine; and glycine; hypocholesteremic agents such as nicotinic acid; the D-isomer of 3,3',5-triiodothyronine; thyroxine-like compounds such as sodium L-thyroxin and sodium D-thyroxine; triiodothyropropionic acid; nafoxidine hydrochloride, 5-methylpyrazole-3-carboxylic acid and 3-methyl-5-isoxazolecarboxylic acid; fecal softeners such as poloxalkol and dioctyl sodium sulfosuccinate; as well as unsaturated fatty acids such as linoleic acid, arachidonic acid and linolenic acid. Although not preferred, edible vegetable oils such as corn oil and safflower oil are also suitable.

POWDER PACKETS

Linear, unbranched and non-cross-linked poly[-{methyl-(3-trimethylammoniopropyl) imino}trimethylene dichloride] is finely powdered and blended with 1% by weight of lactose powder. Aluminum envelopes containing a paper bag liner are individually filled with 0.55 g. of the mixture and sealed against moisture to prevent caking.

HARD GELATIN CAPSULES

A 250 mg. dose of poly-[{methyl-(3-trimethylammoniopropyl) imino} trimethylene dichloride] containing 1% by weight of lactose as described above is filled into the appropriate size hard gelatin capsules.

Alternatively, a dry filled capsule can be prepared from the following components:

| | |
|---|---|
| poly-[{(methyl-3-trimethylammoniopropyl)imino}-trimethylene dichloride] | 300 mg. |
| corn starch | 150 mg. |
| cab-o-sil (anhydrous silica) | 5 mg. |

If capsules of lower potency are to be prepared, the capsule size can be decreased or additional corn starch or other diluent employed. When using smaller amounts of active ingredient it is anticipated that a multiple capsule dose can be administered.

COMPRESSED TABLETS

A dry blend is prepared with the following components:

| | |
|---|---|
| poly-[{(methyl-(3-trimethylammoniopropyl)imino}-trimethylene dichloride] | 1 kg. |
| sucrose, powdered | 30 gms. |
| collidal silica | 10 gms. |
| carbowax-4000 | 30 gms. |

Four thousand tablets are pressed therefrom by direct compression each of which tablets contains 250 mg. of the ionene polymer.

Likewise, compressed tablets are prepared such that each tablet contains:

| | |
|---|---|
| poly-[{(methyl-(3-trimethylammoniopropyl)imino}-trimethylene dichloride] | 300 mg. |
| corn starch | 30 mg. |
| polyvinylpyrrolidone | 10 mg. |
| magnesium stearate | 3 mg. |

After tableting, a plastic film can be applied to the tablets to seal them from moisture in ways well known in the art.

In addition, an enteric coating may be applied, if desired. Such a coating may comprise fats, fatty acids, waxes and mixtures thereof, shellac, ammoniated shellac, and cellulose acid phthalates applied by techniques well known and accepted.

In place of the poly-[{methyl-3-trimethylammoniopropyl)imino} trimethylene dichloride], there may be substituted the other polymer salts of our invention.

Other binding agents may be used in place of sucrose, such as dextrose, lactose, methyl cellulose, natural and synthetic gums, and the like. Talc can replace the calcium or magnesium stearate. A variety of readily available non-toxic anti-caking agents may be substituted for the colloidal silica.

Other lubricants, diluents, binders, coloring agents, flavoring agents and disintegrators can be used as are known in the art employing wet or dry granulation techniques, direct compression, spray drying, and the like.

If desired, a chewable tablet can be prepared from preferably microencapsulated polymer particles by dry granulation as follows:

| | |
|---|---|
| microencapsulated poly-[{(methyl-(3-trimethyl-ammoniopropyl)imino}trimethylene dichloride] | 750 mg. |
| mannitol | 300 mg. |
| sodium saccharine (or other sweetener) | 2 mg. |
| oil of peppermint | 1 mg. |
| carbowax-4000 | 15 mg. |
| microcrystalline cellulose | 100 mg. |

All of the above dosage forms are administered orally in an effective bile acid binding dose. For lowering blood serum cholesterol levels, generally a single or multiple dose of from about 0.1 to 5.0 grams is suitable although doses in excess of 10 grams can be given where indicated. Such doses are also effective in relieving symptoms of biliary pruritus. Administration can be in a variety of forms, such as a suspension, in an aqueous solution, as a chewable or a coated tablet, or in a capsule, and can be continued for an extended course of treatment. Generally, medication is on a daily basis with each day's dose taken in divided portions, preferably with meals.

For control of hypercholesterolemia, the particular individual dosage, given variances in metabolism and diet, is preferably arrived at through an initial determination and continued monitoring of blood serum cholesterol levels. Thus, a moderate dosage might be employed initially, and increased until the desired blood serum cholesterol level is achieved and maintained. For an initial dose, pending such individual adjustment, from 2.5 to 100 mg./kg. of body weight per day is satisfactory.

It is contemplated that acid addition salts of monomer I, as well as acid addition salts of polymer II and III, including those salts derived from the acids $H_{1/m}Y^a$, where Y, m and a are as above defined are equally well suited for the uses heretofore described.

The following examples are included as illustrative of the invention and are not intended to limit the scope of the invention as described in the foregoing specification and claims.

EXAMPLE 1

STEP 1

N,N,N-Trimethyl-[3-(methylamino)-1-propanaminium Bromide Hydrobromide

To a stirred solution of 40% aqueous methylamine 229.57 g. (7.4 moles) cooled in an ice-water bath is added in three equal portions a solution of 3-bromo-N,N,N-trimethyl-1-propanaminium bromide (452.66 g., 1.78 moles) in 400 ml. of distilled water over a period of forty minutes. The ice-water bath is removed and the mixture is stirred for 4.0 hours. After this time the reaction mixture is evaporated under reduced pressure and the crystalline residue is dried in vacuo. Recrystallization of the residue from absolute ethanol gives 442.62 g. (87.6%) of product; m.p. 185°–189° (dec.); NMR (D$_2$O) δ: 2.67 (3H, S, $^+$NH$_2$CH$_3$); 3.16 (9H, S, $^+$N(CH$_3$)$_3$).

Analysis calculated for C$_7$H$_{20}$N$_2$Br$_2$: C, 28.79; H, 6.90; N, 9.59; Br, 54.72. Found: C, 28.63; H, 7.27; N, 9.47; Br, 54.49.

STEP 2

N,N,N-Trimethyl-[3-(methylamino)]-1-propanaminium Bromide

To a stirred suspension of 876.0 g. (3.0 moles) of N,N,N-trimethyl-[3-(methylamino)]-1-propanaminium bromide hydrobromide in 2.75 liters of absolute methanol at room temperature is added a freshly prepared solution of sodium hydroxide (120.0 g., 3.0 moles) in 1.0 liter of absolute methanol over a period of 1.0 hour. The reaction mixture is evaporated under reduced pressure and the solid residue is shaken with 750 ml. of acetonitrile. The insoluble sodium bromide is removed by filtration and the filtrate is evaporated. The solid residue is dried in vacuo to give a quantitative yield of white, crystalline hygroscopic product which may be used without further purification or can be recrystallized from isopropanol-ether. NMR ($D_2O$) $\delta$: 12.28 (3H, S, —$NHCH_3$); 3.11 (9H, S, —$^+N(CH_3)_3$).

STEP 3

3-[N'-(3-Hydroxypropyl)-N'-methylamino]-N,N,N-trimethyl-1-propanaminium Bromide A mixture of 20 g. of oxetane (0.34 mole), 32.8 g. of N,N,N-trimethyl-[3-(methylamino)]-1-propanaminium bromide (0.156 mole) and 22 ml. water is heated in a sealed tube at 100° for 15 hours. The solution is evaporated in vacuo and the residue is dissolved in 50 ml. of acetonitrile and filtered. Upon evaporation the desired product crystallizes. The product may be recrystallized from acetonitrile.

Analysis calculated for $C_{10}H_{25}N_2OBr$: C, 44.61; H, 9.36; N, 10.41; Br, 29.68. Found: C, 44.59; H, 9.02; N, 10.27; Br, 29.84.

STEP 4

3-[N'-(3-Chloropropyl)-N'-methylamino]-N,N,N-trimethyl-1-propanaminium Chloride Hydrochloride A sample of 44.4 g. of product from Step 3, 3-[N'-(3-hydroxypropyl)-N'-methylamino]-N,N,N-trimethyl-1-propanaminium bromide, is dissolved in 500 ml. of water and acidified to pH 2 with concentrated hydrochloric acid. The solution is passed through a column of Dowex 1-X2 chloride form ion exchange resin and the eluant is evaporated under reduced pressure. The residual viscous oil is dried in vacuo and treated with thionyl chloride (25 ml.) added dropwise with stirring during one hour. The solution is heated at 50° for 1.5 hours and then evaporated under reduced pressure.

The residue is washed with ether (2 × 200 ml.) and dried in vacuo. The crude product is dissolved in 100 ml. of water and 0.5 g. of charcoal is added. The mixture is heated to boiling and stirred while hot for one hour. After being filtered through Celite, the filtrate is evaporated under reduced pressure. To the residue is added 40 ml. of isopropanol, which is evaporated. Another 40 ml. of isopropanol is added and the evaporation is repeated until 10 ml. of isopropanol remains. At this point, 100 ml. acetone is added and the product is crystallized. The solid is chopped to a fine powder and collected by suction filtration. The solid is washed with 3:1/acetone: isopropanol (2 × 90 ml.) and acetone (90 ml.). The product is recrystallized from 1:2/isopropanol:acetone to give 30 g. of desire product. Further purification provided the analytical sample.

Analysis calculated for $C_{10}H_{25}N_2Cl_2$: C, 42.95; H, 9.01; N, 10.02; Cl, 38.03. Found: C, 43.07; H, 9.30; N, 10.01; Cl, 38.15.

EXAMPLE 2

3-[N'-(3-Chloropropyl)-N'-methylamino]-N,N,N-trimethyl-1-propanaminium Iodide To a stirred solution of 216.2 mg. (1 mmole) of N,N,N-trimethyl-[3-(methylamino)]-1-propanaminium bromide in 1.5 ml. of acetonitrile is added a solution of 205 mg. (1 mmole) of 3-iodo-1-chloropropane in 0.5 ml. of acetonitrile. The mixture is stirred at room temperature for 2.0 hours and the insoluble N,N,N-trimethyl-[3-methylamino)]-1-propanaminium bromide hydrobromide is removed by filtration. The filtrate is evaporated and the solid residue obtained is extracted with methylene chloride. The methylene chloride extract is evaporated to give the oily product which is recrystallized from isopropanol-ether to afford 90 mg. (52%) of product; m.p. 93° (dec.); NMR $\delta$: 2.2 (3H, S, —$NCH_3$); 3.46 (9H, S, —$^+NMe_3$).

Analysis calculated for $C_{10}H_{24}N_2ClI$: C, 35.89; H, 7.23; N, 8.37; Cl, 10.59. Found: C, 35.75; H, 7.39; N, 8.36; Cl, 10.20.

EXAMPLE 3

3-[N'-(3-Chloropropyl)-N'-methylamino]-N,N,N-trimethyl-1-propanaminium bromide Hydrobromide To a stirred solution of 3.02 g. (14.3 mmoles) of N,N,N-trimethyl-[3-(methylamino)]-1-propanaminium bromide in 30 ml. of acetonitrile is added a solution of 2.25 g. (14.3 mmoles) of 3-bromo-1-chloropropane and the mixture is stirred at room temperature under nitrogen for 3.5 hours. The mixture is cooled in an ice-water bath and then the insoluble material is removed by filtration. The filtrate is evaporated and dried in vacuo and is extracted with chloroform. The chloroform extract is evaporated and dried to give 2.05 g. (100%) of oily product; NMR $\delta$: 2.2 (3H, S, —$NCH_3$); 3.43 (9H, S, —$^+N(CH_3)_3$).

EXAMPLE 4

3-[N'-(3-Iodopropyl)-N'-methylamino]-N,N,N-trimethyl-1-propanaminium Iodide

To a stirred solution of 216.2 mg. (1 mmole) of N,N,N-trimethyl-[3-(methylamino)-1-propanaminium bromide in 1.5 ml. of acetonitrile is added a solution of 296 mg. (1 mmole) 1,3-diiodopropane in 0.5 ml. of acetonitrile. The mixture is stirred at room temperature for 2.0 hours and the insoluble N,N,N-trimethyl-[3-(methylamino)]-1-propanaminium bromide hydrobromide is removed by filtration. The filtrate is evaporated and the solid residue obtained is extracted with methylene chloride. The methylene chloride extract is evaporated to give the oily product which is recrystallized from isopropanol-ether.

EXAMPLE 5

3-[N'-(3-Bromopropyl)-N'-methylamino]-N,N,N-trimethyl-1-propanaminium Bromide Hydrobromide To a stirred solution of 3.02 g. (14.3 mmoles) of N,N,N-trimethyl-[3-(methylamino)-1-propanaminium bromide in 30 ml. of acetonitrile is added a solution of 2.88 g. (14.3 mmoles) of 1,3-dibromopropane and the mixture is stirred at room temperature under nitrogen for 3.5 hours. The mixture is cooled in an ice-water bath and then the insoluble material is removed by filtration. The filtrate is evaporated and dried in vacuo and is extracted with chloroform. The chloroform extract is evaporated and dried to give the product.

EXAMPLE 6

STEP 1

3-(2-Cyanoethyl)aminopropanol

A solution of 75 g. (1 mole) of 3-aminopropanol is stirred while 54 g. (1 mole) of acrylonitrile is added dropwise. After being allowed to stand at room temperature for several hours and preferably overnight, the reaction mixture is concentrated under reduced pressure at 50° yielding 3-(2-cyanoethyl)aminopropanol.

STEP 2

Formate Ester of 3-[N-(2-Cyanoethyl)-N-formylamino]propanol

A solution of 127.7 g. of 3-(2-cyanoethyl)-aminopropanol in 1 liter of 99% formic acid is heated at 85° for 15 hours. The reaction mixture is concentrated under reduced pressure at 80° and the residue is taken up in 60 ml. of methylene chloride-ethyl acetate (1:1). A 1500 g. silica gel G column packed in methylene chlorideethyl acetate is prepared, and the product is purified by adsorption on silica gel G followed by elution using the 1:1 methylene chloride-ethyl acetate system. Concentration of the combined eluates yields the formate ester of 3-[N-(2-cyanoethyl)-N-formylamino]propanol.

STEP 3

3-[N-(2-Cyanoethyl)-N-formylamino]propanol

A solution of 55.7 g. of the formate ester of 3-[N-(2-cyanoethyl)-N-formylamino]propanol in 300 ml. of methanol is treated with 820 mg. of sodium methoxide at room temperature. After 30 minutes, the reaction mixture is concentrated to dryness under reduced pressure and the residue is taken up in 500 ml. of methylene chloride. The methylene chloride solution is filtered and the filtrate is concentrated under reduced pressure yielding 3-[N-(2-cyanoethyl)-N-formylamino]-propanol.

STEP 4

3-[N'-Formyl-N'-(3-hydroxypropyl)amino]-1-propanaminium Chloride

A solution of 15.6 g. (100 mmoles) of 3-[N-(2-cyanoethyl)-N-formylamino]-propanol in 225 ml. of water is treated with 100 ml. of 1 N hydrochloric acid and reduced over 3.8 g. of platinum at room temperature and 40 psi of hydrogen. The reaction mixture is filtered and concentrated under reduced pressure yielding 3-[N'-formyl-N'-(3-hydroxypropyl)amino]-1-propanaminium chloride.

STEP 5

3-[N'-Formyl-N'-(3-hydroxypropyl)amino]-N,N,N-trimethyl-1-propanaminium Chloride To a suspension of 3.6 g. of 3-[N'-formyl-N'-(3-hydroxypropyl)amino]-1-propanaminium chloride in 25 ml. of dimethylformamide is added 10.7 g. of anhydrous sodium carbonate and 33 g. (15 ml.) of iodomethane. The mixture begins to reflux gently. When the initial reaction appears to have subsided, the mixture is stirred an heated at 50° for 18 hours. The reaction mixture is filtered and the filter cake is washed with 3 × 10 ml. portions of dimethylformamide. The combined filtrate and washes is concentrated to dryness under reduced pressure and the residue is taken up in methanol and concentrated to dryness under reduced pressure. The residue is triturated with hot isopropanol and the mixture is filtered. The product is converted to the chloride-ion-containing product by passage by a 5% aqueous solution of the iodidecontaining product through a column of AG1-X2 ion-exchange resin (Cl⁻ cycle) and concentration the aqueous eluate.

STEP 6

3-[N'-(3-Hydroxypropyl)-N'-methylamino]-N,N,N-trimethyl-1-propanaminium Chloride Hydrochloride A mixture of 2 g. of 3-[N'-formyl-N'-(3-hydroxypropyl)amino]-N,N,N-trimethyl-1-propanaminium chloride 4 g. of 99% formic acid and 2 ml. of formalin is stirred and heated at 100° for 17 hours. To the cooled mixture is added 11 ml. of concentrated hydrochloric acid and the reaction mixture is concentrated under reduced pressure. The product is taken up in 35 ml. of 1 N hydrochloric acid and the solution is filtered and concentrated to dryness under reduced pressure yielding 3-[N'-(3-hydroxypropyl)-N'-methylamino]-N,N,N-trimethyl-1-propanaminium chloride hydrochloride.

EXAMPLE 7

Poly-[{methyl-(3-trimethylammoniopropyl)imino-} trimethylene dichloride]

13.25 Grams (47.4 mmoles) of 3-[N'-(3-chloropropyl-N'-methylamino]-N,N,N-trimethyl-1-propanaminium chloride hydrochloride is treated in the cold and under nitrogen with 8.0 ml. of 5.92 N sodium hydroxide (47.4 mmoles). The pH of the mixture is adjusted to 11.9 by the addition of 1 N hydrochloric acid and the solution is separated from salt by centrifugation. The supernatant is transferred to a three-neck flask equipped with a condenser, stirrer and inert gas inlet, and the mixture is stirred and heated to 100° under a nitrogen blanket for 18 hours.

The reaction mixture is diluted to a 200 ml. volume and the solution is placed in an Amicon Filter Cell equipped with a UM 10 Diaflo Ultrafilter. The solution is ultrafiltered at 60 psi until the chloride ion content of the ultrafiltrate is negligible. After 1000 ml. of ultrafiltrate is collected, the retentate is concentrated under reduced pressure and the residue is dried to yield 9.4 g. (81%) of poly-[{methyl-(3-trimethylammoniopropyl)imino}trimethylene dichloride].

EXAMPLE 8

Poly-[{methyl-3-trimethylammoniopropyl)imino-} trimethylene dibromide]

1.689 Grams (4.09 mmoles) of 3-[N'-(3-bromopropyl)-N'-methylamino]-N,N,N-trimethyl-1-propanaminium bromide hydrobromide is treated in the cold and under nitrogen with 0.67 ml. of 6N sodium hydroxide. The mixture is centrifuged, and the supernatant phase is transferred to a sealed tube and heated at 100° for 10 hours in a nitrogen atmosphere. The reaction mixture is diluted to a 100 ml. volume, and the solution is placed in an Amicon Filter Cell equipped with a UM diaflo Ultrafilter. The solution is ultrafiltered at constant volume and 60 psi pressure until the ultrafiltrate gives a negative test for halide (400 ml.). The retentate is concentrate to dryness under reduced pressure yielding 340 mg. of poly-[{methyl-(3-trimethylammoniopropyl)imino} trimethylene dibromide].

EXAMPLE 9

Poly-[{methyl-(3-trimethylammoniopropyl)imino-} trimethylene chloride iodide]

A solution of 7.15 g. (21 mmoles) of 3-[N'-(3-chloropropyl)-N'-methylamino]-N,N,N-trimethyl-1-propanaminium iodide in 3.5 ml. of oxygen-free water is heated at 100° under an argon blanket for 18 hours. The reaction mixture is diluted to a 150 ml. volume, and the solution is placed in an Amicon Filter Cell equipped with a UM 10 Diaflo Ultrafilter. The ultrafiltration is carried out at constant volume and 60 psi pressure. After 900 ml. of ultrafiltrate is collected, the retentate is concentrated at reduced pressure yielding 4.2 g. of poly-[ methyl-(3-trimethylammoniopropyl-)imino trimethylene chloride iodide].

EXAMPLE 10

Poly-[{methyl-(3-trimethylammoniopropyl)imino-} trimethylene diiodide]

A solution of 2.55 g. (6 mmoles) of 3-[N'-(3-iodopropyl)-N'-methylamino]-N,N,N-trimethyl-1-propanaminium iodide in 1 ml. of oxygen-free water is heated in a sealed tube and under a nitrogen blanket at 100° for 24 hours. The reaction mixture is diluted to a 200 ml. volume with water, and the solution is placed in an Amicon Filter Cell equipped with a UM 10 Diaflo Ultrafilter and ultrafiltered at constant volume and 60 psi pressure until 1200 ml. of ultrafiltrate is collected. The retentate is concentrated under reduced pressure yielding 1.68 g. of poly-[{methyl-(3-trimethylammoniopropyl)imino}trimethylene diiodide].

EXAMPLE 11

Poly-[{ methyl-(3-trimethylammoniopropyl)imino-} trimethylene chloride bromide]

3.69 Grams (10 mmoles) of 3-[N'-(3-chloropropyl)-N'-methylamino]-N,N,N-trimethyl-1-propanaminium bromide hydrobromide is treated with 1.7 ml. of 5.92 N sodium hydroxide in the cold and under nitrogen and the pH is adjusted to 11.9 by the addition of 1 N hydrochloric acid. The mixture is stirred and heated at 100° for 18 hours under a nitrogen blanket.

The reaction mixture is diluted to a 100 ml. volume with water and placed in an Amicon Filter Cell equipped with UM 10 Diaflo Ultrafilter and ultrafiltered at constant volume and 60 psi pressure until the ultrafiltrate gives a negative test for halide (600 ml.). The retentate is concentrated under reduced pressure yielding 1.5 g. of poly-[{ methyl-(3-trimethylammoniopropyl)imino} trimethylene chloride bromide].

EXAMPLE 12

Catalytic Conversion of Polymer Chloropropyl End Group to Propyl

A mixture of 5.0 g. poly-[{methyl-(3-trimethylammoniopropyl)imino}trimethylene dichloride] bearing chloropropyl end groups (MW by titration = 2546, 2.0 mmoles), 0.5 g. 5% palladium on carbon, 0.446 g. (4.56 mmoles) of potassium acetate and 30 ml. water is shaken in a Parr apparatus under 40 psi hydrogen pressure for 40 hours at 22°. The mixture is filtered through a sintered funnel containing Supercel to remove catalyst. The filtrate is ultrafiltered (UM 2 ultrafilter) to remove low molecular weight molecules and the retentate is evaporated to dryness yielding the product. Molecular weight of this material (determined by end group titration) = 3042.

For analysis, an aliquot of 1.21 g. of the reduction product is dissolved in 8 ml. water and the solution is acidified to pH 4 with 1% nitric acid. Excess silver nitrate solution is added and the precipitated silver chloride is removed by centrifugation. The filtrate is passed through Supercel and then ultrafiltered through an Amicon Diaflo UM 2 ultrafilter. The retentate is concentrated under reduced pressure to give 0.943 g. product, which is analyzed for chlorine content.

Analysis calculated for ionic Cl, 0; covalent Cl, 0%. Found: ionic Cl, 0%; covalent Cl, 0%.

EXAMPLE 13

Conversion of Polymer Terminal Chloropropyl Moiety to 2-Naphthylthioproyl

A mixture of 154.6 mg. of sodium hydroxide and 650.6 mg. of 2-naphthylmercaptan in 3 ml. water is stirred for 0.5 hour at 22°. Solid poly-[{methyl-(3-trimethylammoniopropyl)imino} trimethylene dichloride] bearing terminal chloropropyl moieties (2.548 g., MW by end group titration = 2546) and 7 ml. water are added and stirring is continued for 24 hours. The mixture is filtered and the filtrate is made up to a 50 ml. volume with water and placed in an Amicon Filter Cell equipped with a UM 10 Diaflo Ultrafilter. After 600 ml. of ultrafiltrate is collected, the retentate is concentrated by dryness at reduced pressure yielding polymer containing 2-naphthylthiopropyl end groups.

In place of 2-naphthylmercaptan there can be employed an analogous quantity of methylmercaptan, ethylmercaptan, 3-propylmercaptan, 2-propylmercaptan and 4-butylmercaptan.

EXAMPLE 14

Conversion of the Polymer Chloropropyl Terminal Group to Benzenethiopropyl

A solution of 3.8 g. of poly-[{methyl-(3-trimethylammoniopropyl)imino} trimethylene dichloride] bearing chloropropyl terminal groups in 6 ml. of water is purged with nitrogen and 441 mg. (0.41 ml.) of benzenethiol and 4 ml. of 1N sodium hydroxide is added. The mixture is stirred under a nitrogen blanket at room temperature for 24 to 40 hours. The mixture is then treated with 5 ml. of 1N hydrochloric acid and extracted three times with 30 ml. portions of ether. The aqueous phase is concentrated to dryness under reduced pressure yielding 3.7 g. of product that is dissolved in 100 ml. of water and ultrafiltered through a UM 2 Diaflo Ultrafilter at constant volume and a pressure of 60 psi. After 1200 ml. of ultrafiltrate is collected, the retentate is concentrated to dryness under reduced pressure yielding 3.27 g. of polymer in which the 3-chloropropyl end groups are converted to 3-benzenethiopropyl end groups.

EXAMPLE 15

Conversion of the Polymer Chloropropyl End Groups to Trimethylammoniopropyl

A solution of 2.7 g. of poly-[{ methyl-(3-trimethylammoniopropyl)imino}trimethylene dichloride] bearing chloropropyl terminal groups in 5 ml. of water is treated with 25 ml. of aqueous 6.4 M trimethylamine at room temperature. After 24 hours, the reaction mixture is concentrated to dryness at 30° C. and reduced pressure. The product is either ground to a powder and dried under reduced pressure or dissolved in 50 ml. of water and ultrafiltered through a UM 2 Diaflo Ultrafilter at constant volume and a pressure of 60 psi until trimethylamine is no longer detected in the ultrafiltrate. Concentration of the retentate under reduced pressure yields 2.7 g. of product in which the 3-chloropropyl end groups are converted to 3-trimethylaminopropyl end groups.

Similarly, other triloweralkylamines such as triethylamine, tripropylamine, tributylamine can also be employed as well as mixtures of the various triloweralkylamines.

What is claimed is:

1. A compound of the formula:

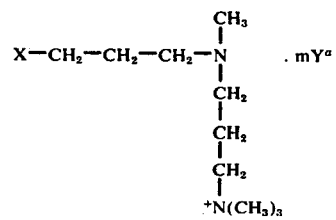

where X is chloro, bromo, or iodo, and y is chloride, bromide, iodide or a pharmaceutically acceptable anion were $a$ is the anionic charge on Y, $m$ is a number such that the product of $m$ and $a$ is 1, and hydroholic acid addition salts thereof.

2. A compound according to claim 1 where X is bromo.
3. A compound according to claim 1 where X is chloro.
4. A compound according to claim 1 where X is iodo.
5. A compound according to claim 1 where Y is bromide.
6. A compound according to claim 1 where Y is chloride.
7. A compound according to claim 1 where Y is iodide.
8. A compound according to claim 2 where Y is bromide.
9. A compound according to claim 3 where y is chloride.
10. 3-[N'-(3-chloropropyl)-N'-methylamino]-N,N,N-trimethyl-1-propanaminium chloride hydrochloride.

* * * * *